US007718680B2

(12) United States Patent
Pellecchia et al.

(10) Patent No.: US 7,718,680 B2
(45) **Date of Patent: *May 18, 2010**

(54) INHIBITION OF LETHAL FACTOR PROTEASE ACTIVITY FROM ANTHRAX TOXIN

(75) Inventors: Maurizio Pellecchia, San Diego, CA (US); Alex Strongin, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 1107 days.

This patent is subject to a terminal disclaimer.

(21) Appl. No.: 11/233,924

(22) Filed: Sep. 23, 2005

(65) Prior Publication Data

US 2008/0033025 A1 Feb. 7, 2008

Related U.S. Application Data

(60) Provisional application No. 60/612,403, filed on Sep. 23, 2004.

(51) Int. Cl.
*A61K 31/426* (2006.01)

(52) U.S. Cl. .................................................... 514/369

(58) Field of Classification Search ....................... None
See application file for complete search history.

(56) References Cited

U.S. PATENT DOCUMENTS

| | | | | |
|---|---|---|---|---|
| 4,559,157 | A | 12/1985 | Smith et al. | |
| 4,608,392 | A | 8/1986 | Jacquet et al. | |
| 4,820,508 | A | 4/1989 | Wortzman | |
| 4,938,949 | A | 7/1990 | Borch et al. | |
| 4,992,478 | A | 2/1991 | Geria | |
| 2005/0187409 | A1 * | 8/2005 | Powers et al. | 564/147 |

OTHER PUBLICATIONS

Dragon et al., The Canadian Veterinary Journal, vol. 36, May 1995, pp. 295-301.*

"Table II—FDA-Approved Commercially Marketed Salts", *Remington's Pharmaceutical Sciences*, (17th Edition), Gennaro, A. R., Editor, Mack Publishing Company, Easton, PA 18042,(1985), p. 1418.

Bradley, K. A., et al., "Identification of the Cellular Receptor for Anthrax Toxin", *Nature*, 414, (Nov. 2001), 225-229.

Buolamwini, J. K., et al., "CoMFA and CoMSIA 3D QSAR and Docking Studies on Conformationally-Restrained Cinnamoyl HIV-1 Integrase Inhibitors: Exploration of a Binding Mode at the Active Site", *Journal of Medicinal Chemistry,* 45, (2002) ,841-852.

Bush, B. L., et al., "Sample-Distance Partial Least Squares: PLS Optimized for Many Variables, With Application to CoMFA", *Journal of Computer-Aided Molecular Design,* 7(5), (Oct. 1993), 587-619.

Cornell, W. D., "A Second Generation Force Field for the Simulation of Proteins, Nucleic Acids, and Organic Molecules", *Journal of the American Chermical Society*, 117(19), (1995), 5179-5197;(Additions and Corrections, Journal of American Chemical Society, 118(9), (1996), p. 2309).

Cramer, III, R. D., et al., "Comparative Molecular Field Analysis (CoMFA). 1. Effect of Shape on Binding of Steroids to Carrier Proteins", *Journal of the American Chemical Society*, 110(18), (1988), 5959-5967.

Dalvit, C., et al., "A General NMR Method for Rapid, Efficient, and Reliable Biochemical Screening", *Journal of American Chemical Society*, 125(47), (2003), 14620-14625.

Duesbery, N. S., et al., "Proteolytic Inactivation of MAP-Kinase-Kinase by Anthrax Lethal", *Science*, 280(5364), (May 1, 1998), 734-737.

Forino, M., et al., "Efficient Synthetic Inhibitors of Anthrax Lethal Factor", *Proc. Natl. Acad. Sci.,* USA, 102(27), (Jul. 5, 2005), 9499-9504.

Hajduk, P. J., et al., "One-Dimensional Relaxation- and Diffusion-Edited NMR Methods for Screening Compounds That Bind to Macromolecules", *Journal of American Chemical Society,* 119(50), (1997),12257-12261.

Hanna, P., "Anthrax Pathogenesis and Host Response", *Current Topics in Microbiology and Immunology,* vol. 225, (1998), 13-35.

Hanna, P. C., et al., "On the Role of Macrophages in Anthrax", *Proc. Natl. Acad. Sci. USA,* 90, (1993),10198-10201.

Huffman, M. A., et al., "Lithium Alkoxides of Cinchona Alkaloids as Chiral Controllers for Enantioselective Acetylide Addition to Cyclic *N*-Acyl Ketimines", *Journal of Organic Chemistry*, 60, (1995), 1590-1594.

Jahnke, W., et al., "Spin Label Enhanced NMR Screening", *Journal of American Chemical Society*, 123(13), (2001), 3149-3150.

Jones, G., et al., "Development and Validation of a Genetic Algorithm for Flexible Docking", *Journal of Molecular Biology*, 267(3), (1997), 727-748.

Jozwiak, K., et al., "Interaction of Noncompetitive Inhibitors With an Immobilized α3β4 Nicotinic Acetylcholine Receptor Investigated by Affinity Chromatography, Quantitative—Structure Activity Relationship Analysis, and Molecular Docking", *Journal of Medicinal Chemistry,* 47, (2004),4008-4021.

Lacova, M., et al., "Effect of Microwave Irradiation on the Condensation of 6-Substituted 3-Formylchromones With Some Five-Membered Heterocyclic Compounds", *Molecules*, 5, (2000), 167-178.

Leppla, S. H., "Anthrax Toxin Edema Factor: A Bacterial Adenylate Cyclase That Increases Cyclic AMP Concentrations in Eukaryotic Cells", *Proc. Natl. Acad. Sci. USA*, 79, (May 1982), 3162-3166.

Madhavan, G. R., et al., "Synthesis and Biological Activity of Novel Pyrimidinone Containing Thiazolidinedione Derivatives", *Bioorganic & Medicinal Chemistry*, 10, (2002), 2671-2680.

Madkour, H. M., et al., "Behavior of Some Activated Nitriles Toward Barbituric Acid, Thiobarbituric Acid and 3-Methyl-1-Phenylpyrazol-5-one", *Molecules*, 5, (2000), 746-755.

Mayer, M. , et al., "Characterization of Ligand Binding by Saturation Transfer Difference NMR Spectroscopy", *Angew. Chem. International Edition*, 38(12), (1999),1784-1788.

(Continued)

*Primary Examiner*—Laura L. Stockton
(74) *Attorney, Agent, or Firm*—Schwegman, Lundberg & Woessner, P.A.

(57) ABSTRACT

The present invention provides compounds that efficiently and specifically inhibit lethal factor (LF) protease activity of anthrax toxin.

6 Claims, 5 Drawing Sheets

OTHER PUBLICATIONS

Meyer, B., et al., "NMR Spectroscopy Techniques for Screening and Identifying Ligand Binding to Protein Receptors", *Angew. Chem. International Edition,* 42(8), (2003), 864-890.

Pan, D., et al., "Constructing Optimum Blood Brain Barrier QSAR Models Using a Combination of 4D-Molecular Similarity Measures and Cluster Analysis", *Journal of Chemical Information and Computer Science*, 44, (2004), 2083-2098.

Park, J. M., et al., "Macrophage Apoptosis by Anthrax Lethal Factor Through p38 Map Kinase Inhibition", *Science*, 297(5589), (Sep. 20, 2002), 2048-2051.

Pellecchia, M., et al., "NMR in Drug Discovery", *Nature Reviews*, 1(3), (Mar. 2002), 211-219.

Pellecchia, M., et al., "NMR-Based Structural Characterization of Large Protein-Ligand Interactions", *Journal of Biomolecular NMR,* 22, (2002),165-173.

Pellizzari, R., et al., "Anthrax Lethal Factor Cleaves MKK3 in Macrophages and Inhibits the LPS/IFNγ-induced Release of NO and TNFα", *FEBS Letters*, 462(1-2), (Nov. 26, 1999), 199-204.

Petosa, C. , et al., "Crystal Structure of the Anthrax Toxin Protective Antigen", *Nature,* 385, (Feb. 1997), 833-838.

Schwarze, S. R., et al., "Protein Transduction: Unrestricted Delivery Into All Cells?", *Trends in Cell Biology,* 10(7), (Jul. 1, 2000), 290-295.

Schymkowitz, J. W., et al., "Prediction of Water and Metal Binding Sites and Their Affinities by Using the Fold-X Force Field", *Proc. Natl. Acad. Sci. USA*, 102(29), (Jul. 19, 2005), 10147-10152.

Scobie, H. M., et al., "Human Capillary Morphogenesis Protein 2 Functions as an Anthrax Toxin Receptor", *Proc. Natl. Acad. Sci. USA*, 100(9), (Apr. 29, 2003), 5170-5174.

Sellman, B. R., et al., "Dominant-Negative Mutants of a Toxin Subunit: An Approach to Therapy of Anthrax", *Science,* 292, (Apr. 27, 2001),695-697.

Smith, H. , et al., "Observations on Experimental Anthrax: Demonstration of a Specific Lethal Factor Produced in vivo by *Bacillus anthracis", Nature*, 173(4410), (May 8, 1954), 869-870.

Stennicke, H. R., et al., "Caspases: Preparation and Characterization", *Methods: A Companion to Methods in Enzymology*, 17, (1999), 313-319.

Stewart, J. J., "Optimization of Parameters for Semiempirical Methods I. Method", *Journal of Computational Chemistry*, 10(2), (1989), 209-220.

Teschner, M. , et al., "Texture Mapping: A New Tool for Molecular Graphics", *Journal of Molecular Graphics*, 12(2), (1994), 98-105.

Tucker, T. J., et al., "Synthesis of a Series of 4-(Arylethynyl)-6-chloro-4- cyclopropyl-3,4-dihydroquinazolin-2(1*H*)-ones as Novel Non-nucleoside HIV-1 Reverse Transcriptase inhibitors", *Journal of Medicinal Chemistry*, 37, (1994), 2437-2444.

Vitale, G. , et al., "Anthrax Lethal Factor Cleaves the N-Terminus of MAPKKs and Induces Tyrosine/Threonine Phosphorylation of MAPKs in Cultured Macrophages", *Biochemical and Biophysical Research Communications*, 248(3), (1998), 706-711.

Vitale, G. , et al., "Susceptibility of Mitogen-Activated Protein Kinase Kinase Family Members to Proteolysis by Anthrax Lethal Factor", *Thd Biochemical Journal.,* 352(3), (2000),739-745.

Wang, G.-W. , et al., "Solvent-Free and Aqueous Knoevenagel Condensation of Aromatic Ketones With Malononitrile", *ARKIVOC*, vol. 2004, Part (ix), (2004),4-8.

Zhou, Z. , et al., "CoMFA 3D-QSAR Analysis of HIV-1 RT Nonnucleoside Inhibitors, TIBO Derivatives Based on Docking Conformation and Alignment", *Journal of Chemical Information and Computer Science*, 44(6), (2004), 2167-2178.

* cited by examiner

INHIBITION OF LETHAL FACTOR PROTEASE ACTIVITY FROM ANTHRAX TOXIN

RELATED APPLICATION

This application claims priority to U.S. Provisional Patent Application Ser. No. 60/612,403, filed Sep. 23, 2004, which is incorporated herein by reference.

GOVERNMENT FUNDING

The invention described herein was made with government support under Grant Number 5UO1-AI056385 awarded by the National Institute of Health. The United States Government has certain rights in the invention.

BACKGROUND OF THE INVENTION

Currently, there is a need for agents to treat harmful bacterial diseases such as, for example, anthrax disease. *Bacillus anthracis* (Smith, H., Keppie, J. *Nature* 173, 869-870 (1954)) is considered the causative bacterium of anthrax disease, whose clinical presentation and outcome in humans strongly depend on its way of entry. Generally, cutaneous contact is rarely lethal, while inhalation is more dangerous and serious. Usually inhalation is fatal if not diagnosed early (Hanna, P. Curr. Topics Microbiol. Immunol. 225, 13-35 (1998)). In fact, in mammals infected with anthrax, bacterium spores germinate in alveolar macrophages before migrating to lymph nodes where they multiply (Hanna, P., Acosta, D., Collier, R. J. Proc. Natl. Acad. Sci. USA 90, 10198-10201 (1993)). Vegetative bacteria excrete a tripartite exotoxin constituted by three different polypeptides: protective antigen (PA, 83 kDa), lethal factor (LF, 90 kDa) and edema factor (EF, 89 kDa). Concerted activity of the above three polypeptides succeeds in killing host cells (Bradley, K. A., Mogridge, J., Mourez, M., Collier, R. J., Young, J. A. Nature 414, 225-229 (2001)). PA (Petosa, C., Collier, R. J., Klimpel, K. R., Leppla, S. H., Liddington, R. C. *Nature* 385, 833-838 (1997)) can bind to an ubiquitously expressed cellular receptor and, after a proteolytic activation, it is cleaved into a 63-kD fragment (PA63) and a 20-kDa (PA20) moiety. PA20 dissociates into medium and allows the PA63 fragment to heptamerize and bind both LF and EF. The resulting complex is engulfed into intracellular compartments called endosomes; this is successively followed by translocation of LF and EF into cytosol (Scobie, H. M., Rainey, G. J., Bradley, K. A., Young, J. A. *Proc. Natl. Acad. Sci. USA* 100, 5170-5174 (2003)). Once inside the cell LF and EF exert their toxic action. EF is a calmodulin-activated adenylyl cyclase that impairs the host defenses through a variety of mechanisms inhibiting phagocytosis (Leppla, S. H. Proc. Natl. Acad. Sci. USA 79, 3162-3166 (1982)). LF is a $Zn^{2+}$ dependent protease capable to cleave several mitogen activated protein kinase kinases (MAPKK) (Vitale, G. et al. Biochem. Biophys. Res. Commun. 248, 706-711 (1998); Duesbery, N. S. et al. *Science* 280, 734-737 (1998)). This cleavage leads to macrophage cell lysis through a mechanism of action not completely known so far. Recently, it has been suggested that in LF-exposed macrophages, apoptosis can be a consequence of p38 MAPK inactivation. This is believed to prevent release of chemokines and cytokines so that immune system becomes unable to respond to the pathogen (Park, J. M., Greten, F. R., Li, Z. W., Karin, M. *Science* 297, 2048-2051 (2002)).

The lethal action of anthrax toxin can be neutralized at several stages during its entry into the cell. In fact it would be possible to inhibit PA63 processing, pore assembly or binding to receptor; moreover a successful therapeutic treatment could prevent LF or EF binding or their translocation into the cytosol (Sellman, B. R., Mourez, M., Collier, R. J. *Science* 292, 695-697 (2001)). Nevertheless inhibition of LF protease activity is still the most promising avenue for this harmful disease (Schwarze, S. R., Hruska, K. A., Dowdy, S. F. *Trends Cell Biol.* 10, 290-295 (2000)).

Inhibition of LF protease activity is believed to be a promising avenue for this harmful disease (Schwarze, S. R., Hruska, K. A., Dowdy, S. F. *Trends Cell Biol.* 10, 290-295 (2000)). Thus, a continuing need exists for compounds that inhibit lethal factor (LF) protease activity of anthrax toxin that are useful for therapeutic applications.

SUMMARY OF THE INVENTION

The present invention provides compounds that efficiently and specifically inhibit lethal factor (LF) protease activity of anthrax toxin. Accordingly, there is provided a therapeutic method for inhibiting lethal factor protease activity comprising administering an effective inhibitory amount of a compound a compound of formula (I):

I

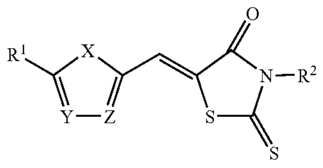

wherein $R^1$ is hydrogen or phenyl, optionally substituted with 1, or 2 substituents independently selected from halo, $—NO_2$, —COOH, or $—SO_2NH_2$;

$R^2$ is hydrogen, $—C_{1-4}$alkyl, $—C_4$alkenyl, —COOH, $—(CH_2)_{1-3}COOH$, $C_{1-6}$alkoxycarbonyl, furyl, furyl$C_{1-3}$ alkylene-, phenyl, (phenyl)$C_{1-3}$alkylene-, or (pyridyl)-$C_{1-3}$alkylene-;

wherein the alkyl, phenyl groups of $R^2$ are optionally substituted with 1, 2, or 3 substituents independently selected from halo, $—OR^a$, $—NO_2$, $—NH_3$, $—SO_2NH_3$, —COOH, $CONH_2$, $—COOCH_3$, $—OCF_3$, or $—CF_3$;

wherein $R^a$ is hydrogen, or $C_{1-4}$alkyl; X, Y and Z are independently non-peroxide —O—, —S—, —NH—, $—CH_2—$, =CH—, or =N—;

or a pharmaceutical acceptable salt thereof.

Additionally, there is provided a therapeutic method for inhibiting lethal factor protease activity comprising administering an effective inhibitory amount of a compound a compound of formula (II):

(II)

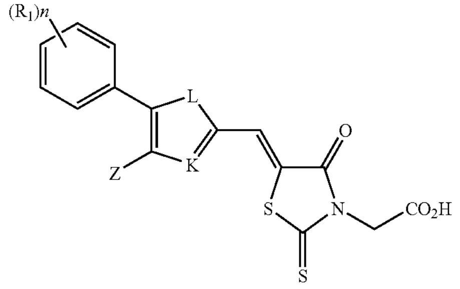

wherein each $R^1$ independently alkyl, alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, cyano, $COOR_7$, $C(=O)R_7$, $NR_7R_8$ or —X—Y—Z;

each Z is independently hydrogen, aryl, heteroaryl, heterocycle or cycloalkyl; optionally substituted with 1, 2 or 3 alkyl, alkoxy, halo, haloalkyl, hydroxy, hydroxyalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $COOR_7$, $C(=O)R_7$, or $NR_7R_8$;

X is O, CO, NH, S or $CH_2$;

Y is O, Co, NH, S or $CH_2$;

L is O, S or NH;

K is O, N, S or CH;

each $R_7$ and $R_8$ are independently hydrogen, alkyl or aryl; and n is 1, 2, 3, 4 or 5;

or a pharmaceutically acceptable salt thereof.

The present invention provides molecules, which show a strong inhibition on LF protease activity in in vitro assays. Accordingly, a therapeutic method is provided for treating a mammal in need of inhibition on LF protease activity, by administering an effective inhibitory amount of a compound of formula (I). In one embodiment the mammal is human.

The invention also provides a therapeutic method to inhibit lethal factor (LF) protease activity of anthrax toxin comprising contacting the cell, in vitro or in vivo, with an effective amount of a compound of formula (I) (as described herein).

The invention provides a compound of formula (I) for use in medical therapy (preferably for use in treating lethal factor (LF) protease activity of anthrax toxin as well as the use of a compound of formula (I) for the manufacture of a medicament for the treatment of a pathological condition or symptom in a mammal, such as a human, which is associated with lethal factor (LF) protease activity from anthrax.

The invention also provides a method of identifying an agent that inhibits the lethal factor (LF) protease activity of anthrax toxin, comprising: a) identifying detecting a selective lethal factor (LF) protease inhibitor; b) contacting a bound lethal factor (LF) protease inhibitor with a test compound, said test compound suspected of being able to inhibit lethal factor (LF) protease; and c) detecting dissociation of said lethal factor (LF) protease inhibitor from said labeled BCl-$X_L$, whereby said candidate agent is identified as an agent that inhibits BCl-$X_L$. The invention provides novel compounds having formula (I).

DETAILED DESCRIPTION

Figure 1A:
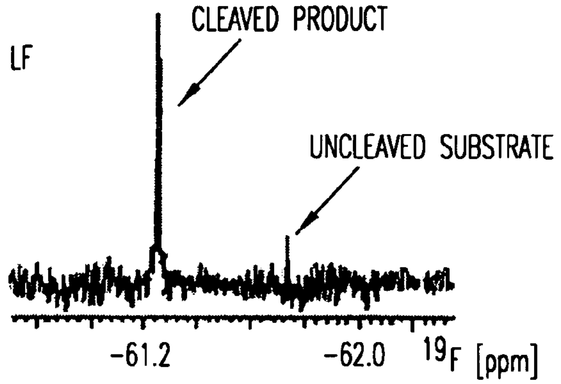
FIG. 1 illustrates the efficacy of our compounds compared with GM6001 in inhibiting LF cleavage of a fluorinated peptide. The detections method is 19F NMR spectroscopy.

As used herein, the following terms and expressions have the indicated meanings. It will be appreciated that the methods of the present invention can employ and/or provide compounds that can contain asymmetrically substituted carbon atoms, and can be isolated in optically active or racemic forms. It is well known in the art how to prepare optically active forms, such as by resolution of racemic forms or by synthesis, from optically active starting materials.

All chiral, diastereomeric, racemic forms and all geometric isomeric forms of a structure are intended, unless the specific stereochemistry or isomeric form is specifically indicated. The processes to prepare or manufacture compounds useful in the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multi-kilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

One diastereomer of a compound disclosed herein may display superior activity compared with the other. When required, separation of the racemic material can be achieved by HPLC using a chiral column or by a resolution using a resolving agent such as camphonic chloride as in Tucker, et al., *J. Med. Chem.,* 37:2437 (1994). A chiral compound described herein may also be directly synthesized using a chiral catalyst or a chiral ligand, e.g. Huffman, et al., *J. Org. Chem.,* 60:1590 (1995).

The present invention is intended to include all isotopes of atoms occurring on the compounds useful in the present invention. Isotopes include those atoms having the same atomic number but different mass numbers. By way of general example and without limitation, isotopes of hydrogen include tritium and deuterium. Isotopes of carbon include C-13 ($^{13}C$) and C-14 ($^{14}C$).

DEFINITIONS

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano. When a substituent is keto (i.e., =O) or thioxo (i.e., =S) group, then 2 hydrogens on the atom are replaced.

The term "alkyl" refers to a monoradical branched or unbranched saturated hydrocarbon chain preferably having from 1 to 8 carbon atoms. This term is exemplified by groups such as methyl, ethyl, n-propyl, iso-propyl, n-butyl, iso-butyl, sec-butyl, n-hexyl, and the like.

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_x$ or $COOR_x$, wherein each $R_x$ is independently H or alkyl.

The alkyl can optionally be interrupted with one or more non-peroxide oxy (—O—), thio (—S—), sulfonyl (SO) or sulfoxide ($SO_2$).

The alkyl can optionally be at least partially unsaturated, thereby providing an alkenyl or alkynyl.

The term "alkoxy" refers to the groups alkyl—O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more alkyl, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkoxy, halo, haloalkyl, hydroxy, hydroxyalkyl, aryl, heteroaryl, heterocycle, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkoxy, halo, haloalkyl, hydroxy, hydroxyalkyl, aryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "heterocycle" refers to a saturated or partially unsaturated ring system, containing at least one heteroatom selected from the group oxygen, nitrogen, and sulfur, and optionally substituted with alkyl or $C(=O)OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkoxy, halo, haloalkyl, hydroxy, hydroxyalkyl, aryl, heteroaryl, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula $[-(CH_2-)_aA-]$ where a is equal to or greater than 2, and A at each separate occurrence can be O, N, S or P. Examples of crown compounds include, by way of example only, $[-(CH_2)_3-NH-]_3$, $[-((CH_2)_2-O)_4-((CH_2)_2-NH)_2]$ and the like. Typically such crown compounds can have from 4 to 10 heteroatoms and 8 to 40 carbon atoms.

The term "alkanoyl" refers to C(=O)R, wherein R is an alkyl group as previously defined.

The term "acyloxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to C(=O)OR, wherein R is an alkyl group as previously defined.

The term "amino" refers to $-NH_2$, and the term "alkylamino" refers to $-NR_2$, wherein at least one R is alkyl and the second R is alkyl or hydrogen. The term "acylamino" refers to RC(=O)N, wherein R is alkyl or aryl.

The term "nitro" refers to $-NO_2$.

The term "trifluoromethyl" refers to $-CF_3$.

The term "trifluoromethoxy" refers to $-OCF_3$.

The term "cyano" refers to —CN.

The term "hydroxy" or "hydroxyl" refers to —OH.

The term "oxy" refers to —O—.

The term "thio" refers to —S—.

As to any of the above groups, which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

Obviously, numerous modifications and variations of the present invention are possible in light of the above teachings. It is therefore to be understood that within the scope of the appended claims, the invention may be practiced otherwise than as specifically described herein.

Regarding a compound of formula (I):

A specific value for $R^1$ is nitrophenyl, halophenyl, dihalophenyl, carboxy-phenyl, or halonitrophenyl.

A more specific value for $R^1$ is dichlorophenyl, fluorophenyl, iodophenyl, carboxy-phenyl, chlorocarboxy-phenyl, or halonitrophenyl.

A specific value for $R^2$ is hydrogen, $CF_3$-phenyl, $-C_{1-3}$ alkenyl, $-(CH_2)_{1-3}COOH$, $-CH_2CH_2COOH$, $-CH_2CH_2CH_2COOH$, nitrophenyl, furyl-$C_{1-2}$alkylene-, sulfamoyl-phenyl, (phenyl)$C_{1-2}$alkylene-, or (pyridyl)$C_{1-2}$ alkylene-, benzyl or phenylethyl, Cl, $CF_3$-phenyl, $CH_3O-$, Cl-phenyl.

A more specific value for $R^2$ is hydrogen, $—CH_2CH{=}CH_2$, $—CH_2CH_2COOH$, $CH_2CH_2CH_2COOH$, nitrophenyl, pyridylmethyl-, furylmethyl-, or benzyl.

Specific values for X, Y and Z are —O—, =CH— and =N— respectively.

A specific value for each $R^a$ is methyl.

A specific group of compounds are compounds of formula (I) are illustrated in table I; or a pharmaceutically acceptable salts thereof.

TABLE I

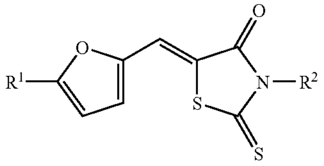

I

| Compound | $R_1$ | $R_2$ | $IC_{50}$ |
|---|---|---|---|
| BI-9B9b | H | $—CH_2COOH$ | 140.0 μM |
| 1 | 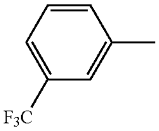 | 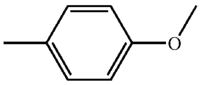 | 300.0 μM |
| 2 | 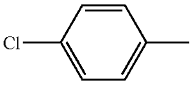 | 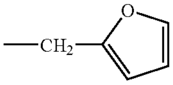 | 150 μM |
| 3 | 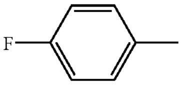 | $—CH_2CH{=}CH_2$ | 50.0 μM |
| 4 | 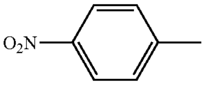 | 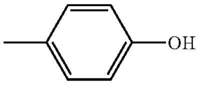 | 37.7 μM |
| 5 | 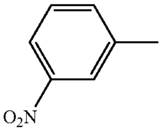 | 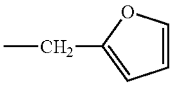 | 36.3 μM |
| 6 | 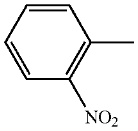 | 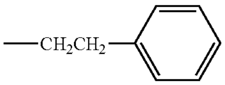 | 31.9 μM |
| 7 | 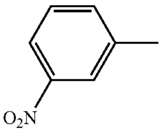 | $—CH_2CH_2CH_2COOH$ | 20.0 μM |
| 8 | 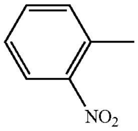 | $—CH_2CH_2COOH$ | 12.8 μM |
| 9 | 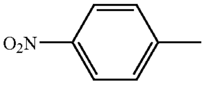 | 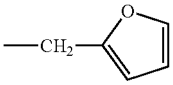 | 12.6 μM |

TABLE I-continued
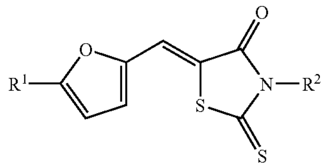
I
| Compound | $R_1$ | $R_2$ | $IC_{50}$ |
| --- | --- | --- | --- |
| 10 | 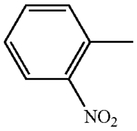 | $—CH_2COOH$ | 12.5 μM |
| 11 | 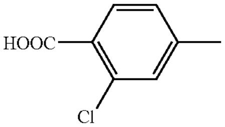 | 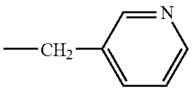 | 9.9 μM |
| 12 | 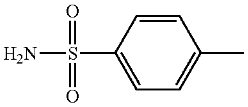 | $—CH_2COOH$ | 9.1 μM |
| 13 | 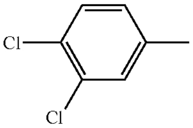 | H | 7.4 μM |
| 14 | 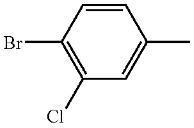 | H | 7.0 μM |
| 15 | 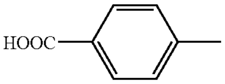 | 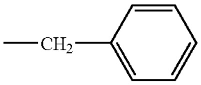 | 6.0 μM |
| 16 | 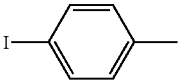 | $—CH_2COOH$ | 5.5 μM |
| 17 | 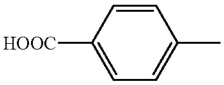 | 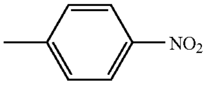 | 4.8 μM |
| 18 | 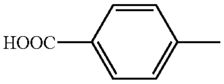 | 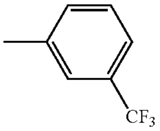 | 2.9 μM |
| 19 | 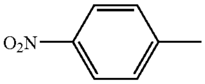 | $—CH_2CH_2COOH$ | 2.7 μM |
| 20 | 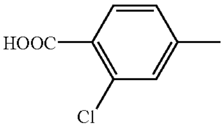 | $—CH_2CH{=}CH_2$ | 2.7 μM |

TABLE I-continued

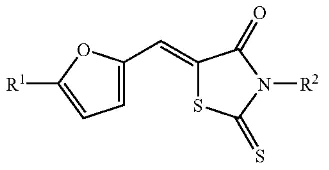

I

| Compound | $R_1$ | $R_2$ | $IC_{50}$ |
|---|---|---|---|
| 21 | 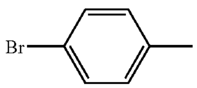 | $—CH_2CH_2CH_2COOH$ | 2.3 μM |
| BI-MFM3 | 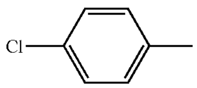 | $—CH_2CH_2COOH$ | 1.7 μM<br>Ki = 0.8 ± 0.3 μM |

The compounds of the invention can be prepared using standard techniques known to those skilled in the art. Many of these compounds are commercially available from a chemical supplier, such as Maybridge, Chembridge and Chemnavigator (San Diego, Calif.) Compounds in Table II can be synthesized by methods known in the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably n the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to inhibit LF protease activity may be determined using pharmacological models which are well known to the art, or using the procedures described below.

The compounds of the invention can be evaluated for the ability to block proteolytic activity of Lethal Factor, using NMR- and fluorescence-based enzymatic assays. LF specifically cleaves proteins of the MAPK-kinase family ( ) Vitale, G., Bernardi, L., Napolitani, G., Mock, M., Montecucco, C. *Biochem. J* 352, 739-745 (2000) at their amino termini (Pellizzari, R., Guidi-Rontani, C., Vitale, G., Mock, M., Montecucco, C. *FEBS Lett.* 462, 199-204 (1999)). The optimized peptide MAPKKide™ (List Biological Laboratories, Inc.) was used as a substrate for the fluorescence assays.

MAPKKide™ is derived from the MAPKK-2 substrate for LF and it is intramolecularly quenched by fluorescence resonance energy transfer. The C-terminally-linked fluorophore is a fluorescein-thiocarbamoyl (FITC) and the acceptor chromophore is DABCYL 4-{[4(Dimethylamino)-phenyl]-azo}-benzoic acid. After cleavage of LF it is possible to detect a sensible fluorescence increasing in reaction solution setting excitation and emission wavelengths at 485 and 590 nm, respectively.

The fluorescence-based assay used in the invention is known to those skilled in the art, and is a useful technique to search for very potent inhibitors. It is not unambiguous in detecting weaker ligands (>100 μM) because of possible interference between the test compounds (normally used at high concentration) and the spectrophotometric assay. Therefore, a NMR-based binding and enzymatic assay, which was less likely to lead to false positive (Pellecchia, M., Sem, D. S., Wuthrich, K. *Nature Reviews* 1, 211-219 (2002); Meyer, B., Peters, T. *Angew. Chem. Int. Ed.* 42, 864-890 (2003); Wuthrich, K. *NMR of Protein and Nucleic Acids*. (Wiley, New York, 1986); Pellecchia, M. et a. *J. Biomol. NMR* 22, 165-173 (2002) and Hajduk, P. J., Olejniczak, E. T., Fesik, S. W. *J. Am. Chem. Soc.* 123, 3149-3150 (2001)).

Mayer, M., Meyer, B. *Angew. Chem. Int. Edn. Engl.* 38, 1784-1788 (1999)) results was employed. Recently, it has been reported that $^{19}$F-1D NMR experiments were successful in the detection of enzyme activity and inhibition both in proteases and kinases (Dalvit, C., Ardini, E., Flocco, M., Fogliatto, G. P., Mongelli, N. et al. *J. Am. Chem. Soc.* 125, 14620-14625 (2003)). NMR experiments based on observation of $^{19}F$ provide several benefits. The $^{19}F$ nucleus shows a sensitivity comparable to that of $^1H$ so that it is possible to acquire 1D spectra in a relatively short time. Moreover because of its large anisotropy $^{19}F$ chemical shifts are spread over a wide spectral window; as a consequence the potential spectral resolution is greatly improved. It is also worthy to underline that overlapped signals unlikely occur in NMR spectra, considering that $^{19}F$ is not very common biologically (Pellecchia, M., Crowell, K. J., Fragai, M., Fattorusso, R., Tautz, L., Mustelin, T., Zhang, Z. Y., Snipas, S., Boatright, K., Salvesen, G. Submitted).

LF inhibition was detected using $^{19}F$-NMR, and the fluorinated peptide Ac-A-R-R-K-K-V-Y-P-NH-Ph-$CF_3$ was used as an enzymatic substrate. The shift of $^{19}F$ NMR signal (towards lower field) was observed. It is believed that this shift is due to the above enzymatic reaction. Cleavage of the peptide occurring at the Pro position is believed to affect the chemical environment of $^{19}F$ nuclei because of the conversion of the amide functionality into a p$CF_3$-aniline.

The strategy was applied to a small but diversified library of about 300 compounds representing most of the scaffolds commonly found in drugs. The results of the testing identified four weak scaffolds showing high macromolar inhibitory activity for LF. The activity of focus on compound BI-9B9b, was analyzed first because it exerted an interesting 50% LF inhibition at 140 μM concentration in both NMR- and fluorescence-based assays.

Exploring commercially available compounds from companies, such as Maybridge, Chembridge and those listed by Chemnavigator (San Diego, Calif.), the most representative derivatives of BI-9B9b (twenty-two among about 680 analogues) were selected. The test compounds, reported in Table I, were analyzed and, apart from compounds 1 and 2, all showed a much stronger inhibitory activity against LF than BI-9B9b. Particularly, compounds BI-MFM3, 13, 14, 15, 16 and 17 emerged as very effective inhibitors with a >70% LF inhibition at 10 μM concentration.

Figure 1B:
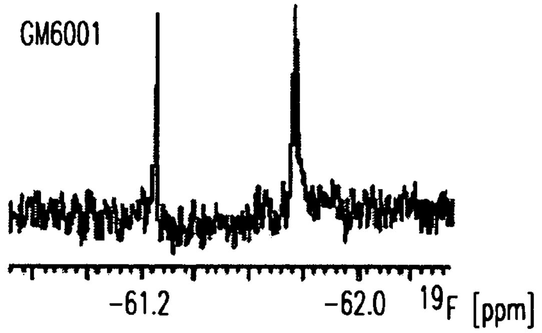
Figure 1C:
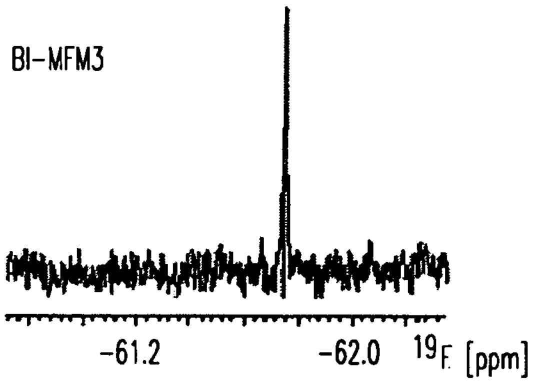

NMR analysis was used to confirm the enzymatic activity of the compounds of the invention. For each of compound, a $^{19}F$-1D NMR experiment was performed. The detection of LF enzymatic reaction by $^{19}F$ NMR is shown (FIG. 1). In FIG. 1A) a strong NMR signal relative to p$CF_3$-aniline produced by the cleavage of the fluorinated peptide (20 μM) by lethal factor (10 μM) after 30 minutes. FIG. 1B) illustrate the same reaction carried out in presence of the LF peptide inhibitor GM6001 (20 μM), used as a reference compound (Stennicke, H. R., Salvesen, G. S. *Methods* 17, 313-319 (1999)). In the FIG. 1B spectrum it can be seen that LF activity was reduced by approximately half by GM6001. Finally, the same reaction using BI-MFM3 (20 μM) as an inhibitor was conducted. The results from testing BI-MFM3 are illustrated in FIG. 1C. This Figure illustrates the results of the enzymatic reaction conducted in presence of our test compound, BI-MFM3. Only the $^{19}F$ NMR signal relative to uncleaved peptide appears. Thus, BI-MFM3 shows an inhibitory activity about twice as strong as GM6001.

The compounds effective against anthrax lethal factor, by NMR-based assay, were analyzed using kinetic studies. The $IC_{50}$ of the test compounds was determined. The LF catalyzed hydrolysis of MAPKKide™ in the presence of inhibitor was detected in the same assay buffer and experimental conditions reported above. In addition, inhibitory activity of each compound was measured at six different inhibitor concentrations (1, 5, 10, 20, 50, 100 μM). The $IC_{50}$ values are shown in Table I.

Figure 2:
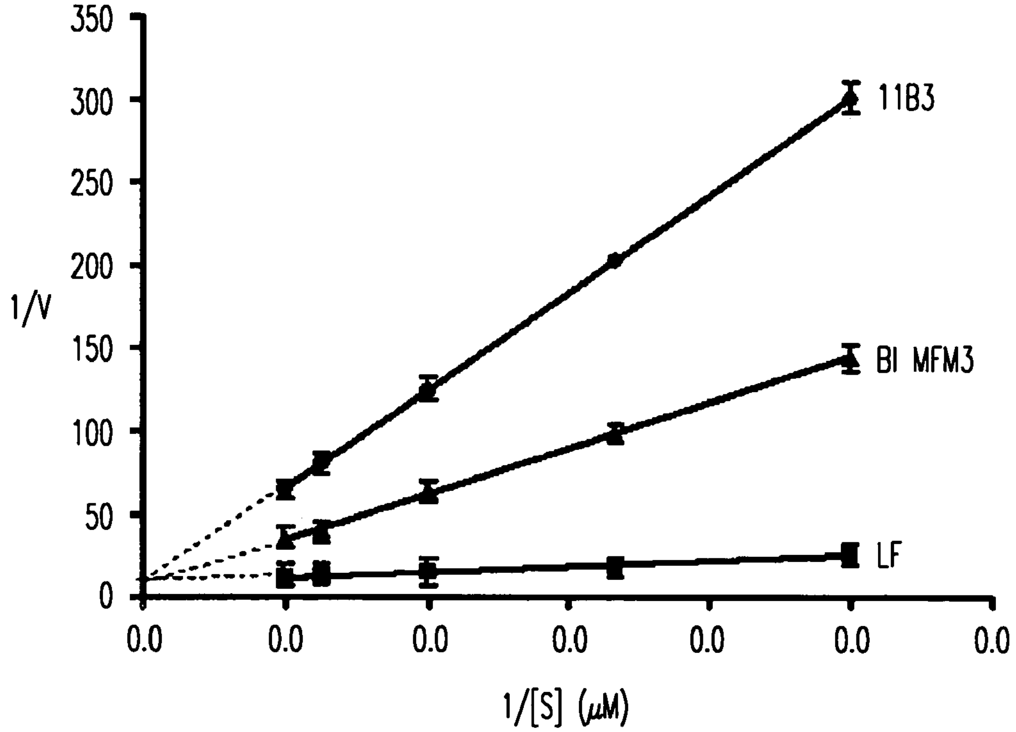
FIG. 2 illustrates the Ki values for compounds BI-MFM3 (Table I) and compound BI-11B3 (Table II).

For compound BI-MFM3, besides its $IC_{50}$, the Ki value and type of inhibition were also evaluated (FIG. 2). A fluorescent-based assay was performed to determine kinetic constants for the LF-catalyzed hydrolysis of MAPKKide™. The experimental conditions described herein were used but the peptide concentration was modified. The velocity of the enzymatic reaction was measured at 2, 3, 5, 8 and 10 μM peptide concentrations. $K_m$ and $V_{max}$ values for the above enzymatic reaction resulted to be 2.22±0.2 μM and 0.0942±0.0007 μmol $min^{-1}$ $mg^{-1}$ of LF, respectively. A superimposable assay was performed using a fixed concentration of BI-MFM3 (10 μM) in each well. The exact Ki value (0.8±0.3 μM) for compound BI-MFM3 was determined and to establish its inhibition as a competitive one, since no effect on the $V_{max}$ was detected and an increasing in $K_{m(app)}$ value (0.38±0.4 μM) was observed.

According to the data obtained (Table I) the presence in $R^1$ position of a substituted phenyl with a small electronegative group significantly increases inhibitory activity, while a small group containing a carboxylic moiety in position $R^2$ seems to improve the potency. On the contrary, a large group such as a substituted phenyl in $R^2$ causes a dramatic reduction of activity especially if not balanced with an effective group in $R^1$.

Figure 1D:
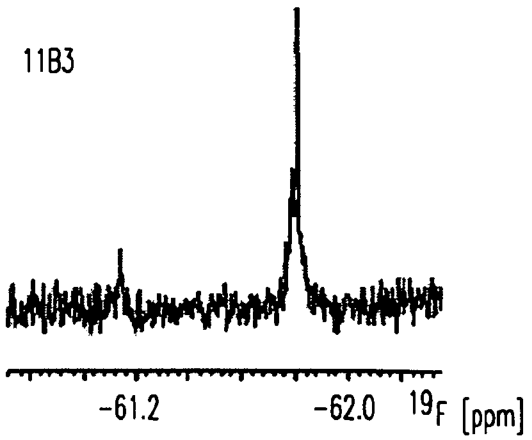

In particular a comparison of the activities for compounds 8 and 17 suggested that an acetyl group would be the preferred substituent in $R^2$ Regarding $R^1$ group substitutions in all position on the phenyl ring seem to be equally effective, thus indicating that compounds with multiple substituents on $R^1$ may result in an increased activity. To verify this hypothesis a synthetic scheme was developed to afford additional BI-MFM3 analogues, that were subsequently tested against LF as reported in table 2. In agreement with our observation each of the synthesized compounds showed a much stronger activity than BI-MFM3 both in the enzymatic and NMR-based assay. In particular, compound BI-11B3 appeared to be the most potent inhibitor with a very low Ki value (32 nM), as illustrated in FIG. 2. NMR-based assay also highlighted the potent LF inhibition due to compound BI-11B3 (FIG. 1D).

Figure 3:
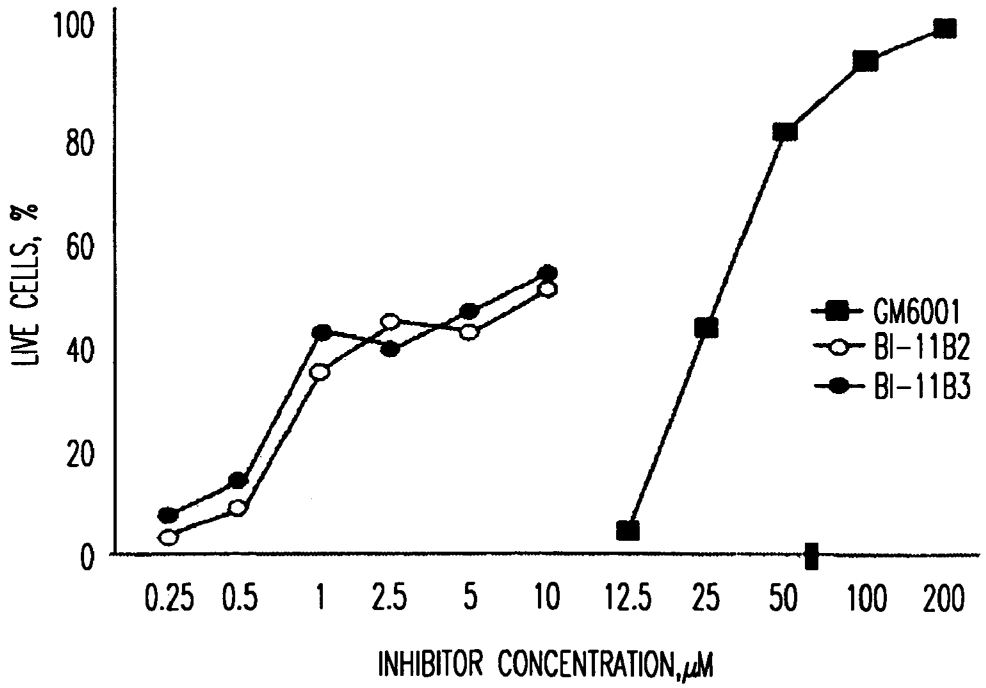
FIG. 3 illustrates the efficacy of compounds BI-11B2, BI-11B1 in protecting cell=death induced by LF in macrophages.

Finally cell-based assay was performed on the three most potent synthetic compounds, namely BI-11B1, BI-11B2 and BI-11B3. As shown in FIG. 3 all of them effectively protect macrophages from LF-PA induced cell death at concentration as low as 1 μM therefore 100 fold more potent than GM6001.

TABLE 2

| Compound | % yield | $IC_{50}$ (Ki) |
|---|---|---|
| 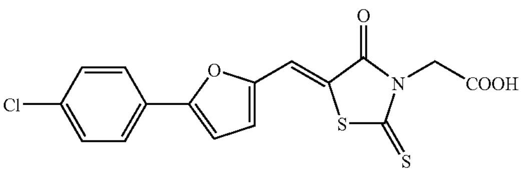 BI-11A9 | 88 | 0.9 μM |

TABLE 2-continued

| Compound | % yield | $IC_{50}$ (Ki) |
|---|---|---|
| 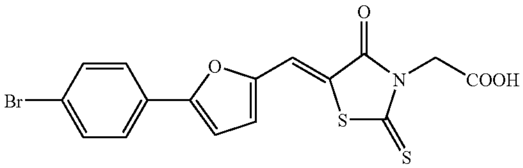 BI-11A10 | 89 | 0.85 μM |
| 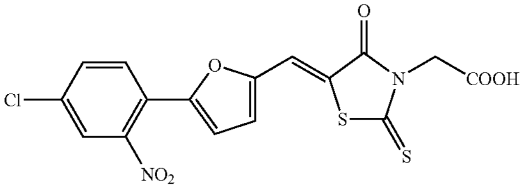 BI-11A11 | 53 | 500 nM |
| 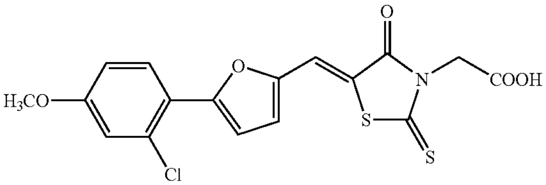 BI-11B1 | 83 | 298 nM |
| 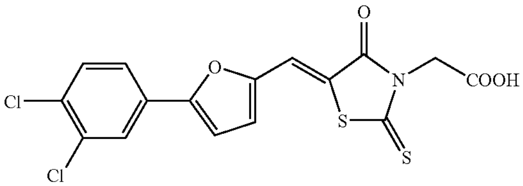 BI-11B2 | 30 | 265 nM |
| 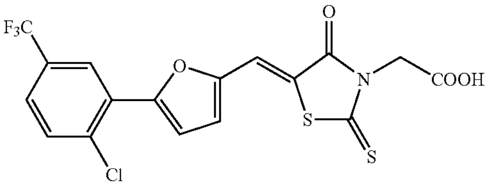 BI-11B3 | 66 | 195 nM (32 nM) |

Figure 4:
FIG. 4. X-ray structure of BI-MF3 in complex with LF.

X ray crystallography was used to obtain further insights on the mechanism of action of our compounds we have also afforded a 3D structure of compound BI-MFM3 in complex with LF (FIG. 4). Analysis of the docked structure revealed that rhodanine ring is capable to interact with $Zn^{2+}$ metal-ion via the thiozolidine sulfur atom, which explained the activity of the scaffold BI-9B9b (Table 1) against LF and other MMPs. In addition, hydrophobic interactions between the $R_1$ group and hydrophobic side groups of LF were also observed and are believed likely to be responsible for the increased affinity and selectivity of our compounds for LF versus other MPPs.

With the long term goal of developing novel potential treatments for Anthrax disease, we previously identified several small molecule inhibitors that inhibit Anthrax LF protease activity with $IC_{50}$'s in sub-micromolar range. Forino, M.; Johnson, S.; Wong, T. Y.; Rozanov, D. V.; Savinov, A. Y.; Li, W.; Fattorusso, R.; Becattini, B.; Orry A. J., Jung D.; Abagyan, R. A.; Smith, J. W.; Alibek, K.; Liddington, R. C.; Strongin, A. Y.; Pellecchia M. Efficient synthetic inhibitors of anthrax lethal factors *Proc Natl Acad Sci U S A.* 2005, 102, 9499-504. Cell based and peptide cleavage assays were subsequently used to confirm the potency of the iterate leads. The most potent compounds were subsequently tested in mice models of the diseases showing a protection against *Bacillus anthracis* spores, when used in combination with the antibiotic ciproflaxin. Forino, M.; Johnson, S.; Wong, T. Y.; Rozanov, D. V.; Savinov, A. Y.; Li, W.; Fattorusso, R.; Becattini, B.; Orry A. J., Jung D.; Abagyan, R. A.; Smith, J. W.; Alibek, K.; Liddington, R. C.; Strongin, A. Y.; Pellecchia M. Efficient synthetic inhibitors of anthrax lethal factors *Proc Natl Acad Sci U S A.* 2005, 102, 9499-504. Initial structure activity relationship (SAR) data suggested that the presence of multiple substitutions on the phenyl ring significantly increases the inhibitory activity. Forino, M.; Johnson, S.; Wong, T. Y.; Rozanov, D. V.; Savinov, A. Y.; Li, W.; Fattorusso, R.; Becattini, B.; Orry A. J., Jung D.; Abagyan, R. A.; Smith, J. W.; Alibek, K.; Liddington, R. C.; Strongin, A. Y.; Pellecchia M.

Figure 5:
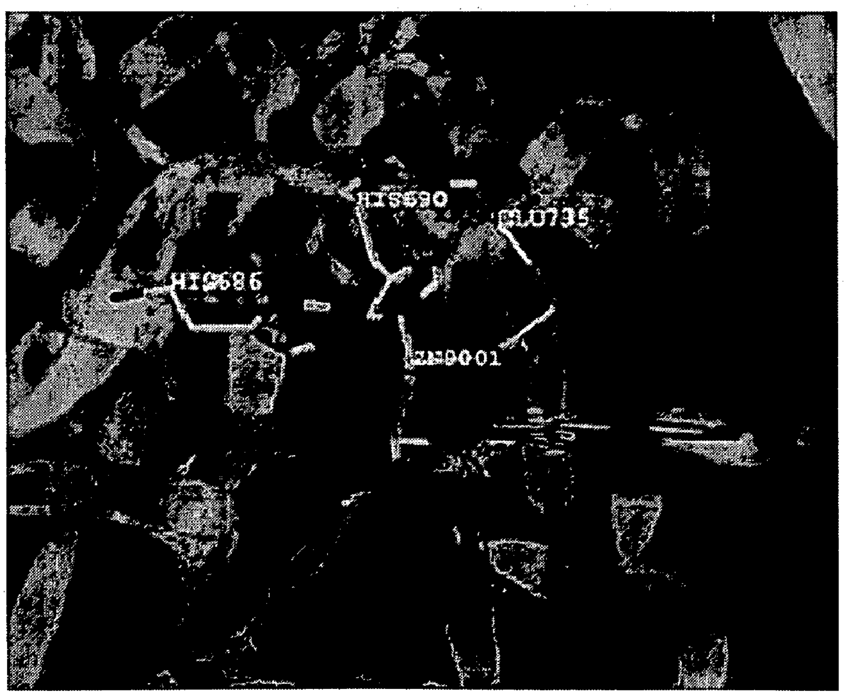
FIG. 5 illustrates a detail of the X-ray structure of compound BI-MFM3 in complex with LF (PDB_ID 1ZXV).

Efficient synthetic inhibitors of anthrax lethal factors *Proc Natl Acad Sci U S A.* 2005, 102, 9499-504. Furthermore, details of the 3D structure of the complex between LF and a representative compound, BI-MFM3 revealed that the rhodanine ring is capable of interacting with $Zn^{2+}$ metal-ion via the thiazolidinedione sulfur atom (FIG. 5). Forino, M.; Johnson, S.; Wong, T. Y.; Rozanov, D. V.; Savinov, A. Y.; Li, W.; Fattorusso, R.; Becattini, B.; Orry A. J., Jung D.; Abagyan, R. A.; Smith, J. W.; Alibek, K.; Liddington, R. C.; Strongin, A. Y.; Pellecchia M. Efficient synthetic inhibitors of anthrax lethal factors *Proc Natl Acad Sci U S A.* 2005, 102, 9499-504.

In this work, we report on further synthesis and SAR studies in which we explored the relative importance of various chemical substructures of BI-MFM3 in inhibiting the protease activity of LF. In this respect, exploration of substituting the rhodanine ring with thiazolidinedione, thiobarbituric acid, creatinine and creatinine acetic acid was investigated. In addition, we synthesized a set of analogues in which we varied the nature of the phenyl and furan rings, as well (Tables 3 and 4). The synthesis of each compound was achieved in part as described in our previous work (Forino, M.; Johnson, S.; Wong, T. Y.; Rozanov, D. V.; Savinov, A. Y.; Li, W.; Fattorusso, R.; Becattini, B.; Orry A. J., Jung D.; Abagyan, R. A.; Smith, J. W.; Alibek, K.; Liddington, R. C.; Strongin, A. Y.; Pellecchia M. Efficient synthetic inhibitors of anthrax lethal factors *Proc Natl Acad Sci U S A.* 2005, 102, 9499-504) by preparing the appropriate aldehyde derivatives and by using a final condensation step using the Knoevenagel reaction. Wang, G-W. and Cheng, B. Solvent-free and aqueous Knoevenagel condensation of aromatic ketones and malonitrile, *Arkivoc* 2004, 5, 4-8. The latter was carried out either under reflux in acetic acid or by using microwave assisted conditions. Madkhur, H. M. F.; Mahmoud M. R.; Nassar, M. H.; Habashy, M. M. Behaviour of Some Activated Nitriles Toward Barbituric Acid, Thiobarbituric Acid and 3-Methyl-1-Phenylpyrazol-5-one *Molecules* 2000, 5, 746-755; Madhavan, G. R.; Chakrabarti, R.; Vikramadithyan, R. K.; Mamidi, R. N. V. S.; Balraju, V.; Rajesh, B. M.; Misra, P.; Kumar, S. K. B.; Lohray, B. B.; Lohray, V. B. and Rajagopalan, R. Synthesis and Biological Activity of Novel Pyrimidinone Containing Thiazolidinedione Derivatives *Bioorg. Med. Chem.* 2000, 10, 2671-2680. Lacova, M.; Gasporova, R.; Loos, D.; Liptay, T.; Pronayova, N. Effect of microwave irradiation on the condensation of 6-substituted 3-formylchromones with some five-membered. heterocyclic compounds. *Molecules* 2000, 5, 167-178.

The compounds were obtained with average yields ranging from 80 to 96%. The details of the experimental conditions are reported as supplementary information. Once synthesized and characterized, we then performed an enzymatic assay to evaluate the inhibitory activity of the resulting compounds against LF. A fluorescence peptide cleavage assay (100 μL) was performed in a 96 well plate. Each reaction consisted of MAPKKide (4 μM) and LF (50 nM) (Lists Biological Laboratories) in 20 mM Hepes, pH 7.4, and the small-molecule inhibitor. Kinetics of the peptide cleavage was examined for 30 min by using a fluorescent plate reader at excitation and emission wavelengths of 485 and 590 nm, respectively, and $IC_{50}$ values were obtained by dose response measurements. For a number of compounds, Lineweaver-Burk analysis was also carried out to verify that the compounds are competitive against the substrate. Forino, M.; Johnson, S.; Wong, T. Y.; Rozanov, D. V.; Savinov, A. Y.; Li, W.; Fattorusso, R.;Becattini, B.; Orry A. J., Jung D.; Abagyan, R. A.; Smith, J. W.; Alibek, K.; Liddington, R. C.; Strongin, A. Y.; Pellecchia M. Efficient synthetic inhibitors of anthrax lethal factors *Proc Natl Acad Sci U S A.* 2005, 102, 9499-504.

Figure 6A:
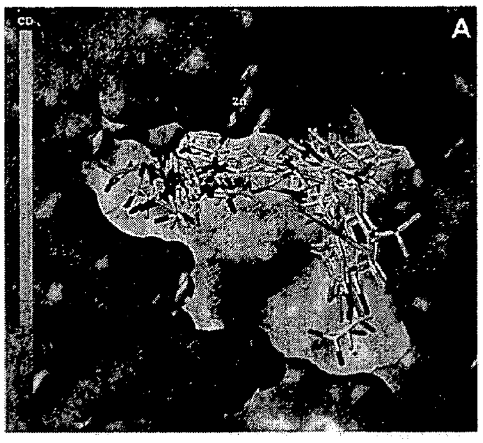
FIG. 6 illustrates a superimpositions of docked conformers used for CoMFA studies. In (A), the structures of the compounds for the training set are displayed, with the compound highlighted in green being BI-MFM3 (whose coordinates are from the PDB_ID 1ZXV). In (B), the aligned structures for the compounds in the test sets are displayed. (C) Calculated versus observed $pIC_{50}$ values against LF for the compounds in the training set ($q^2$=0.51, $r^2$=0.98, # components=4, # compounds=17). (D) Predicted versus observed $pIC_{50}$ values against LF for the 10 compounds in the test set.
Figure 6B:
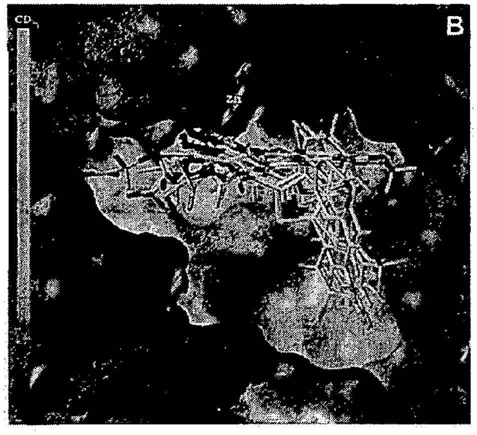
Figure 6C:
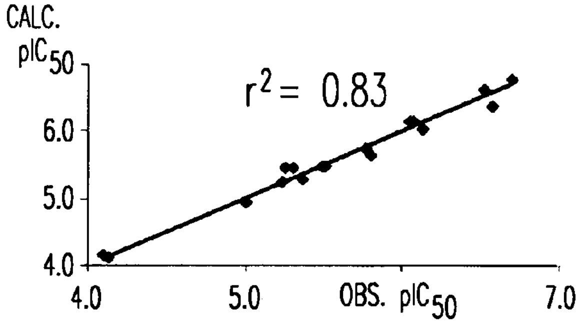
Figure 6D:
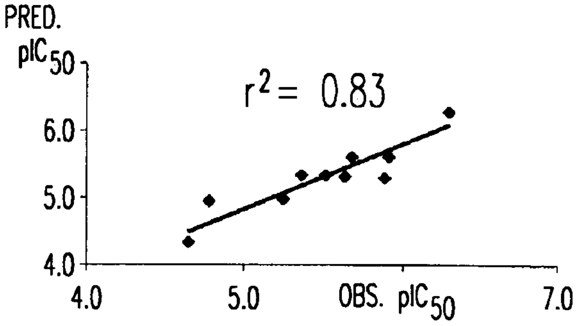
Figure 7A:
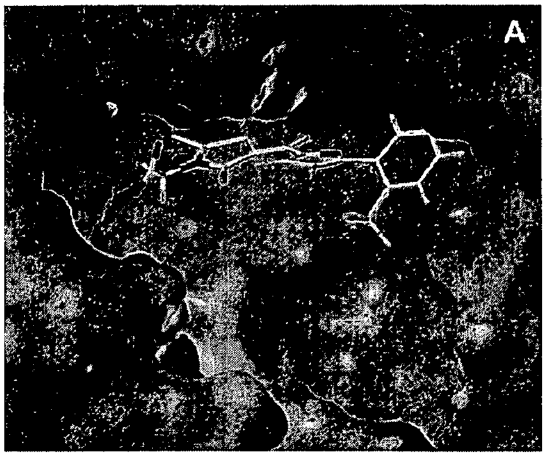
FIG. 7 illustrates the comparison of (A) hydrophobic and hydrophilic potential molecular surface (MOLCAD) (Teschner M.; Henn C.; Vollhardt H.; Reiling S.; Brickmann J. Texture mapping: a new tool for molecular graphics. *J. Mol. Graph.* 1994, 12, 98-105) of the substrate binding site of LF with (B) CoMFA contour plots of steric field contributions. Comparison of the (C) electrostatic potential molecular surfaces (MOLCAD) with (D) CoMFA contour plots of electrostatic field contributions. In (A), the hydrophobic and hydrophilic areas are displayed in brown and blue, respectively, while green surfaces represent an intermediate hydrophobicity. In (B), green contours indicate the regions where the addition of bulky groups may increase activity and yellow contours indicate the regions where the addition of bulky groups may decrease activity. In (C), positive and negative areas are displayed in red and blue, respectively, while cyan surfaces represent neutral areas. The color code follows the definitions of MOLCAD. (Teschner M.; Henn C.; Vollhardt H.; Reiling S.; Brickmann J. Texture mapping: a new tool for molecular graphics. *J. Mol. Graph.* 1994, 12, 98-105.) In (D), blue contours indicate regions where less electronegative groups may increase activity. Red contours indicate regions where more electronegative groups may increase activity.
Figure 7B:
Figure 7C:
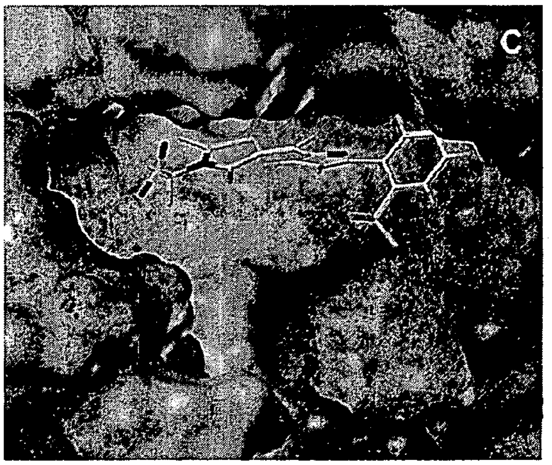
Figure 7D:
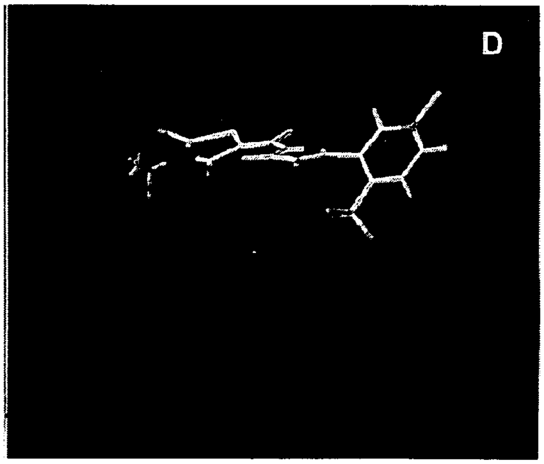

From the data reported in Tables 3 and 4 it appears clear that substitutions of the rhodanine ring gives the most dramatic effects with a severe loss of activity when the ring is substituted with creatinine or creatinine acetic acid moiety. However, substitution with a thiobarbituric acid ring is allowed. The furan ring can also be substituted with thiophene or a thiazole ring without a dramatic effect on the inhibitory affinity of the resulting compounds, while a variety of substitutions on the phenyl ring are very well tolerated. To obtain further insights on the mechanism of action of our compounds we have recently obtained the X-ray high-resolution structure for LF in complex with a representative compound, BI-MFM3 (Forino, M.; Johnson, S.; Wong, T. Y.; Rozanov, D. V.; Savinov, A. Y.; Li, W.; Fattorusso, R.; Becattini, B.; Orry A. J., Jung D.; Abagyan, R. A.; Smith, J. W.; Alibek, K.; Liddington, R. C.; Strongin, A. Y.; Pellecchia M. Efficient synthetic inhibitors of anthrax lethal factors *Proc Natl Acad Sci U S A.* 2005, 102, 9499-504) (FIG. 5). The data reported in Tables 3 and 4 and the X-ray structure of the complex between BI-MFM3 and LF provide a platform that should enable us to identify the chemical determinants for the activity of the compounds. Details of the three-dimensional structure of the complex between LF and BI-MFM3 revealed that the rhodanine ring is able to interact with $Zn^{2+}$ metal-ion via the thiazolidine sulfur atom. It is reasonable to predict that even small changes in this position may largely affect activity. This is observed with closely related compounds in which the rhodanine ring is substituted with a thiazolidinedione ring (for example BI-11D8 and BI-11D9; Tables 3 and 4). Likewise, the activity of thiobarbiturates derivatives could be attributed to the presence of the sulfur atom that could presumably interact similarly with the metal ion. Finally, in such scenario, substitution of the rhodanine ring with a creatinine moiety is predicted to abolish the $Zn^{2+}$-chelating ability of the compounds, with concomitant loss of activity, as indeed observed (Table 3). The carboxylic group of BI-MFM3 is pointing towards a hydrophilic region of the protein close to its surface (FIG. 5), which explains the variability of the substitutions allowed at this position and the increased affinity of the compounds with a small charged group (Table 3 and 2). In addition, hydrophobic interactions between the phenyl ring and hydrophobic side chains of LF were also observed. However, electron density of the benzene ring is less evident in the X-ray structure of BI-MFM3[11] indicating a possible conformational mobility around the carbon-carbon bond of the p-substituted benzene ring and the larger available space around this portion of the ligand. These observations correlate with the higher tolerance of substitutions at this position (Tables 3 and 4). Therefore, analysis of the X-ray structure of BI-MFM3 in complex with LF provides a qualitative interpretation of the structure-activity relationship data reported in Tables 3 and 4. These studies should enable us to design additional compounds with possibly improved affinity, selectivity and drug-likeness. In this respect, having in hand the X-ray structure of a representative compound gives us the possibility to establish an alignment rule for the superposition of the diverse set of derivatives in order to carry out a CoMFA (Comparative Molecular Field Analysis) study. Cramer, R. D-III; Patterson, D. E.; Bunce, J. D. Comparative molecular field analysis (CoMFA). 1. Effect of shape on binding of steroids to carrier proteins. *J. Am. Chem. Soc.* 1988, 110, 5959-5967. It has been shown (Buolamwini, J. K.; Assefa, H.; CoMFA and CoMSIA 3D QSAR and Docking Studies on Conformationally-Restrained Cinnamoyl HIV-1 Integrase Inhibitors: Exploration of a Binding Mode at the Active Site. *J. Med. Chem.* 2002, 45, 841-852; and Zhou, Z.; Madura, J. D. CoMFA 3D-QSAR Analysis of HIV-1 RT Nonnucleoside Inhibitors, TIBO Derivatives-Based on Docking Conformation and Alignment. *J. Chem. Inf. Comput. Sci.* 2004, 44, 2167-2178) that this combined experimental and statistical approach is more robust then using simple in silico docking strategies that are hindered by the lack of suitable force fields and scoring functions especially when the binding site contains metal ions. Schymkowitz, J. W.; Rousseau, F.; Martins, I. C.; Ferkinghoff-Borg, J.; Stricher, F.; Serrano, L. Prediction of water and metal binding sites and their affinities by using the Fold-X force field. *Proc Natl Acad Sci U S A.* 2005, 102, 10147-10152. Docking simulations of our novel inhibitors into the LF binding pocket were performed using GOLD 2.2 (Jones, G.; Willett, P.; Glen, R. C.; Leach, A. R.; Taylor, R. Development and validation of a genetic algorithm for flexible docking. *J. Mol. Biol.* 1997, 267, 727-748.) and by using the GOLD fitness function. Jones, G.; Willett, P.; Glen, R. C.; Leach, A. R.; Taylor, R. Development and validation of a genetic algorithm for flexible docking. *J. Mol. Biol.* 1997, 267, 727-748. All torsion angles in each compound were allowed to rotate freely, but the distance between the LF metal ion and the sulfur atom in each inhibitor was constrained (2.5 Å to 3.0 Å). The starting coordinates of the binding sites were taken from the X-ray crystal structure from our previous work (PDB_ID 1ZXV). The preparation and calculation of molecular coordinates of all molecules and CoMFA studies were carried out using SYBYL7.0 (TRIPOS, St. Louis). SYBYL, version 6.9; Tripos Inc. (1699 South Hanley Road, St. Louis, Mo., 63144). The docked conformations of 17 compounds were used as a training set for the CoMFA study (Table 3, FIG. 6A) while the docked structures for 10 additional compounds were used as a test set (Table 4, FIG. 6B). However, inhibitors with $IC_{50}$ values equal and greater then 100 μM were not included in the CoMFA. Partial charges for the protein (LF) were assigned from the AMBER02 force field (Cornell, W. D.; Cieplak, P.; Bayly, C. I.; Gould, I. R.; Merz, K. M.; Ferguson, D. M.; Spellmeyer, D. C.; Fox, T.; Caldwell, J. W.; Kollman, P. A. A Second Generation Force Field for the Simulation of Proteins, Nucleic Acids, and Organic Molecules. *J. Am. Chem. Soc.* 1996, 118, 2309) and atomic charges for the 27 inhibitors were calculated using PM3 (MOPAC6.0). Stewart, J. J. P. Optimization of parameters for semiempirical methods I. Method. *J. Comp. Chem.* 1989, 10, 209-220. The inhibition constants were expressed in $pIC_{50}$ values ($pIC_{50}=-\log [IC_{50}]$), and correlated with the steric and electrostatic fields (COMFA) as well as the total polar surface area (TPSA) of each compound. Jozwiak, K.; Ravichandran, S.; Collins, J. R.; Wainer, I. W. Interaction of Noncompetitive Inhibitors with an Immobilized 34 Nicotinic Acetylcholine Receptor Investigated by Affinity Chromatography, Quantitative-Structure Activity Relationship Analysis, and Molecular Docking *J. Med. Chem.* 2004, 47, 4008-4021. Pan, D.; Iyer, M.; Liu, J.; Li, Y.; Hopfinger, A. J.; Constructing Optimum Blood Brain Barrier QSAR Models Using a Combination of 4D-Molecular Similarity Measures and Cluster Analysis. *J. Chem. Inf. Comput. Sci.* 2004, 44, 2083-2098. The cross-validation with leave-one-out option and the SAMPLS program, (Bush, B. L.; Nachbar, R. B. Sample-distance partial least-squares PLS optimized for many variables, with application to CoMFA. *J. Comput.-Aided Mol. Des.* 1993, 7, 587-619) rather than column filtering, was carried out to obtain the optimal number of components to be used in the final analysis. After the optimal number of components (four) was determined, a non-cross-validated analysis was performed without column filtering. The $q^2$ (cross-validated $r^2$ of 0.51), SPRESS (cross-validated standard error of prediction of 0.60), $r^2$ (non-cross-validated $r^2$ of 0.98, FIG. 6C), and F values (145.94) were computed according to the definitions in SYBYL. The relative contributions to this CoMFA model were 40.9% for the steric field, 38.5% for electrostatic field, and 20.6% for total polar surface area (TPSA). In order to evaluate the predictive ability of this model, we subsequently calculated the $pIC_{50}$ values for the 10 compounds in the test set (FIG. 6D, Table 4). As it can be seen in FIG. 6D, the model exhibits a remarkably good predictive ability ($r^2=0.83$). The comparison between the CoMFA contours and the docking site for the compounds is reported in FIG. 7 that displays our most active compound, BI-11B3. The comparison of binding site of LF (and its hydrophobic molecular surface) with the CoMFA contour plots of steric field contribution shows a very good agreement (FIGS. 3A,B). Likewise, there is a very good parallel between the electrostatic potential molecular surfaces of the protein with the electrostatic CoMFA contour plots (FIGS. 2C,D). It is also evident that the substrate binding pocket is substantially larger then the compounds particularly around the phenyl group of BI-11B3 (FIG. 7), which may explain the positive TSA contribution to the CoMFA equation. Therefore, by using a combination of medicinal chemistry and computational analysis, aided by experimental X-ray data, we were able to rationalize the activity of the compounds in terms of specific interactions with the LF substrate binding site. The resulting 3D QSAR model provides an invaluable tool to estimate the inhibition constants of additional compounds and could therefore be used to prescreen in silico compounds to be synthesized and tested.

We have generated and validated a first series of LF inhibitors with low- to sub-micromolar activity. By using a structure-based approach, we derived a quantitative model that should enable the design of more potent compounds against LF. For example, BI-11B3 derivatives that are substituted in the phenyl ring with even larger substituents containing less electronegative groups should result much more potent then the parent compounds. The high level of compatibility between the PLS coefficient contour maps from CoMFA with the molecular surface of the active site of LF provides further validation of the proposed model. Ultimately, it would also be interesting to test all the derived compounds against other related human metallo-proteases and carry out a similar CoMFA analysis to establish if elements that are predicted to confer selectivity could be identified. Such analysis could also be very useful for the design of potent and selective compounds against other therapeutically relevant metallo-proteases.

TABLE 3

Inhibitory Activity and Training Set Data for QSAR.

| # BI- | Structure | $IC_{50}$ | $pIC_{50}$ Obs | $pIC_{50}$ Calc |
|---|---|---|---|---|
| 9B9b | 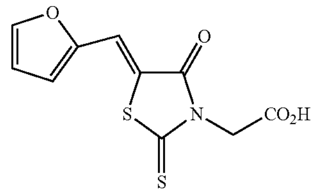 | 140 μM | 3.85 | ND |

TABLE 3-continued
Inhibitory Activity and Training Set Data for QSAR.
| # BI- | Structure | $IC_{50}$ | $pIC_{50}$ Obs | $pIC_{50}$ Calc |
|---|---|---|---|---|
| MFM3 | 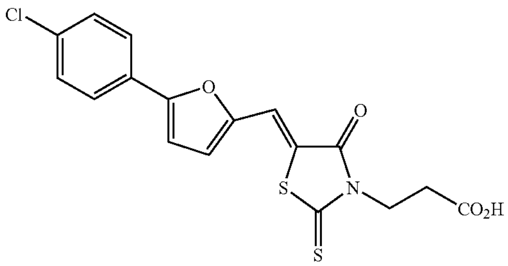 | 1.7 μM | 5.77 | 5.74 |
| 11A9 | 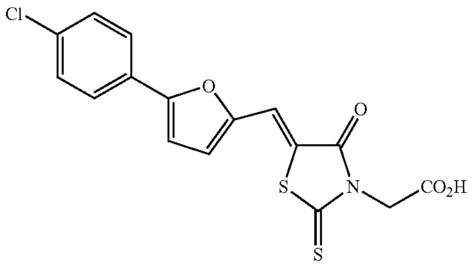 | 0.9 μM | 6.05 | 6.14 |
| 11A10 | 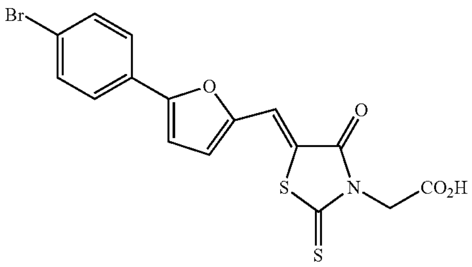 | 0.85 μM | 6.07 | 6.14 |
| 11A12 | 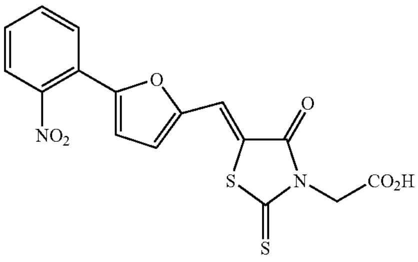 | 3.1 μM | 5.51 | 5.48 |
| 11B1 | 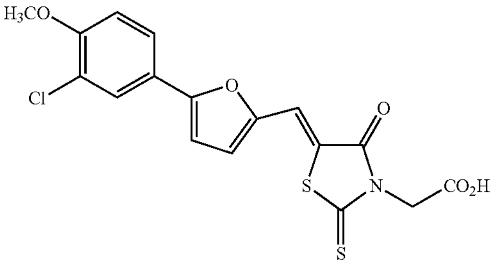 | 0.30 μM | 6.53 | 6.61 |

TABLE 3-continued
Inhibitory Activity and Training Set Data for QSAR.
| # BI- | Structure | $IC_{50}$ | $pIC_{50}$ Obs | $pIC_{50}$ Calc |
|---|---|---|---|---|
| 11B2 | 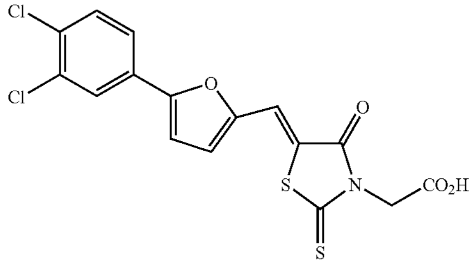 | 0.26 μM | 6.58 | 6.36 |
| 11B3 | 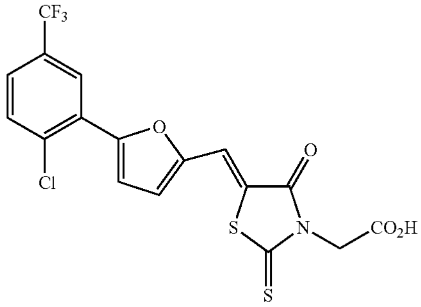 | 0.19 μM | 6.71 | 6.77 |
| 11B10 | 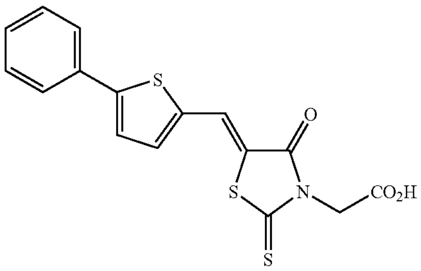 | 0.74 μM | 6.13 | 6.02 |
| 11D1 | 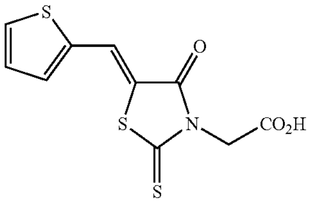 | 79.4 μM | 4.10 | 4.15 |
| 11D10 | 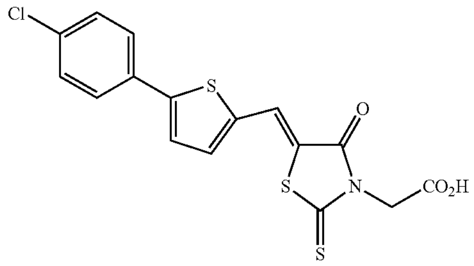 | 3.2 μM | 5.49 | 5.48 |

TABLE 3-continued
Inhibitory Activity and Training Set Data for QSAR.
| # BI- | Structure | $IC_{50}$ | $pIC_{50}$ Obs | $pIC_{50}$ Calc |
|---|---|---|---|---|
| 11E2 | 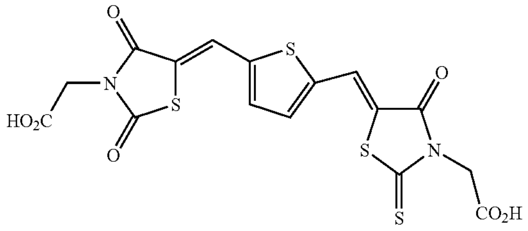 | 1.6 μM | 5.80 | 5.65 |
| 11D2 | 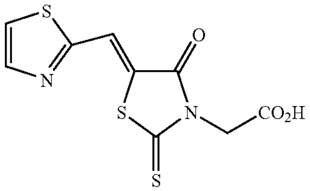 | 72.4 μM | 4.14 | 4.12 |
| 11D5 | 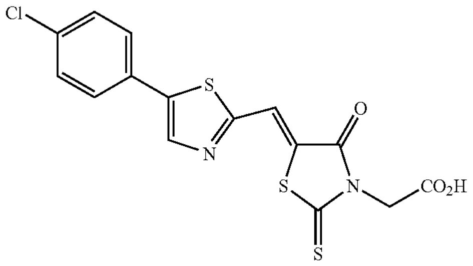 | 10.0 μM | 5.00 | 4.94 |
| 11D6 | 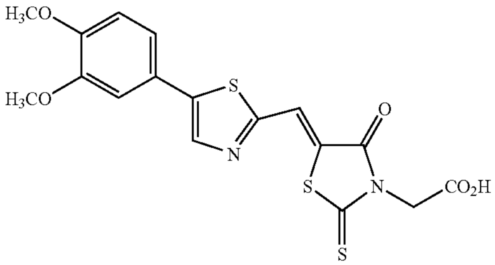 | 5.0 μM | 5.30 | 5.44 |
| 11E4 | 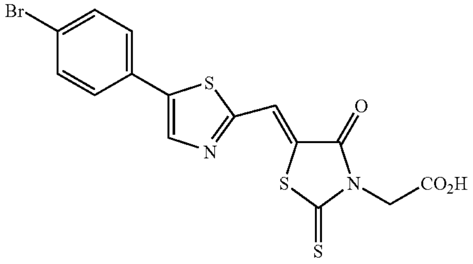 | 4.4 μM | 5.36 | 5.27 |

TABLE 3-continued
Inhibitory Activity and Training Set Data for QSAR.
| # BI- | Structure | $IC_{50}$ | $pIC_{50}$ Obs | $pIC_{50}$ Calc |
|---|---|---|---|---|
| 11D9 | 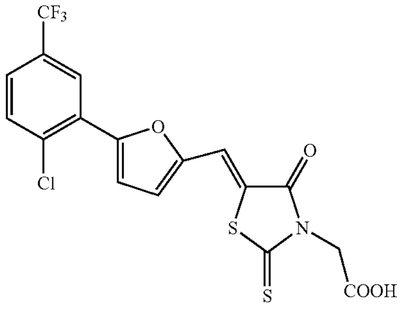 | 5.9 μM | 5.23 | 5.25 |
| 11C5 | 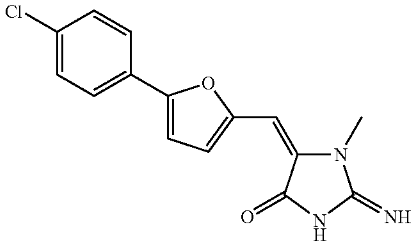 | 200 μM | 3.70 | ND |
| 11B11 | 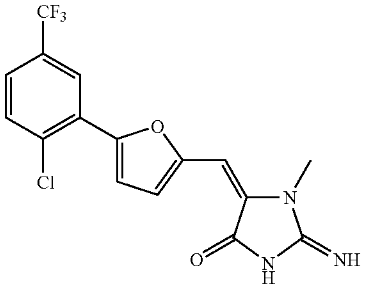 | 100 μM | 4 | ND |
| 11C11 | 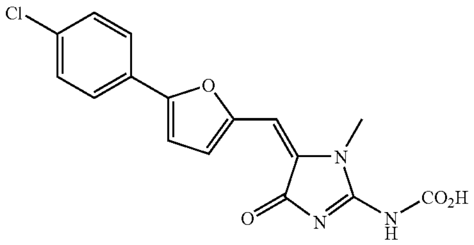 | >100 μM | >4 | ND |

TABLE 4
Inhibitory activity and Test Set Data for the 3D QSAR studies
| # BI- | Structure | $IC_{50}$ | $pIC_{50}$ Obs | $pIC_{50}$ Pred |
|---|---|---|---|---|
| 11C2 | 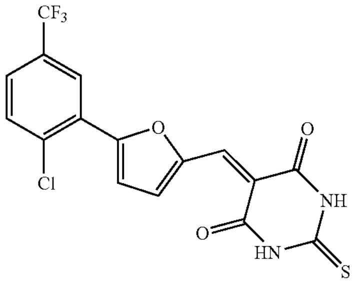 | 1.3 μM | 5.89 | 5.30 |
| 11C3 | 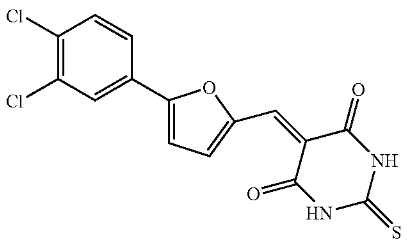 | 2.1 μM | 5.68 | 5.61 |
| 11C4 | 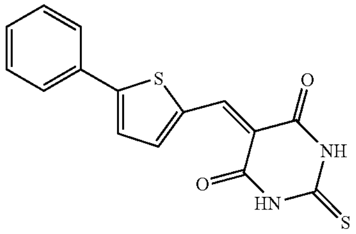 | 1.2 μM | 5.92 | 5.61 |
| 11D3 | 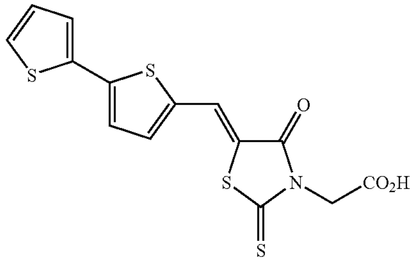 | 2.3 μM | 5.64 | 5.32 |
| 11B12 | 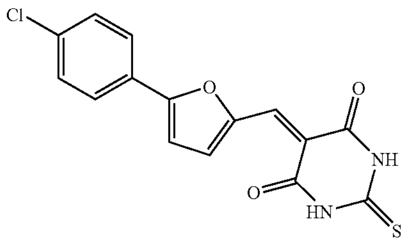 | 4.4 μM | 5.36 | 5.34 |

TABLE 4-continued
Inhibitory activity and Test Set Data for the 3D QSAR studies
| # BI- | Structure | $IC_{50}$ | $pIC_{50}$ Obs | $pIC_{50}$ Pred |
|---|---|---|---|---|
| 11C12 | 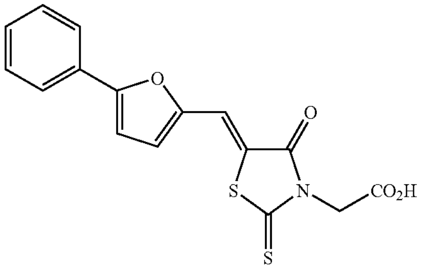 | 16.6 μM | 4.78 | 4.94 |
| 11E3 | 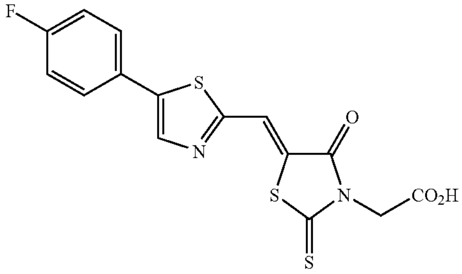 | 22.4 μM | 4.65 | 4.33 |
| 11D8 | 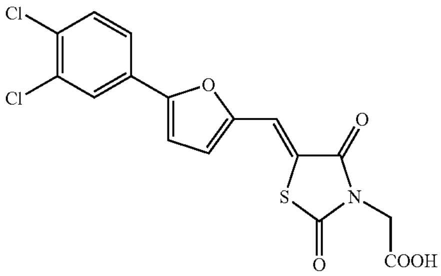 | 5.6 μM | 5.25 | 4.97 |
| 11C1 | 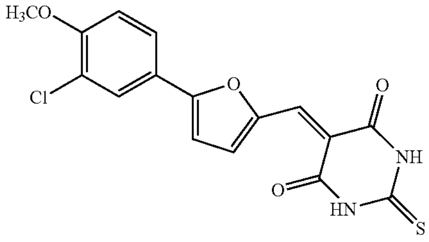 | 3.0 μM | 5.52 | 5.33 |
| 11A11 | 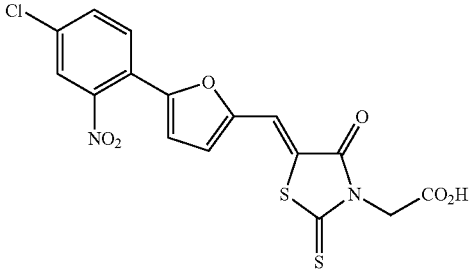 | 0.5 μM | 6.30 | 6.27 |

Materials

All common chemical and buffers were purchased from Sigma-Aldrich. Recombinant LF and MAPKKide™ were both purchased from List Biological Laboratories Inc.; while fluorinated LF-peptide substrate from Anaspec Inc.

Chemical Library

In designing the library the following criteria were adopted: average molecular weight <300; octanol/water repartition coefficient (Log P)<1.3; number of rotatable bonds between 0 and 2. This was made in order to predict favorable outcome in ADME (adsorption, distribution, metabolism, excretion) studies.

Fluorescent Plate-Based Assay

For fluorescence screening 96-well plates were used. Volume of reaction solution was 100 μl per well. To initiate enzymatic reaction LF 50 nM was added to each well containing 20 mM HEPES, pH 7.4, 4 μM MAPKKide™ and 50 μM of test compound. Kinetic measurements were carried out every minute for 30 minutes using a fluorescent plate reader (Finstruments Fluoroskan II). Excitation and emission maxima were 485 and 590 nm, respectively.

$IC_{50}$ evaluation was performed using the same experimental conditions described above but at 30° C. and at inhibitor concentrations of 1, 5, 10, 20, 50, 100 and 200 μM.

The $IC_{50}$ value was determined fitting the data to Sigmoidal dose/response equation and plotting the observed percentage of inhibition versus the logarithm of inhibitor concentration using GraphPad Prism®.

Kinetic constants ($K_m$ and $V_{max}$) were determined at 30° C. adopting the same experimental condition described above for the fluorescence screening assay, but using increasing MAPKKide™ concentration (2, 3, 5, 8 and 10 μM). $K_i$ and $K_{m(app)}$ were calculated always in the same above condition at a fixed 10 μM inhibitor concentration in each well.

All constant values were definitely evaluated by fitting the data to the Lineweaver-Burk equation and plotting inverse value of V (reaction velocity) versus inverse value of MAPKKide™ concentration, using GraphPad Prism®.

NMR Measurements $^{19}F$ NMR 1D spectra were acquired on a Bruker Avance 500 MHz spectrometer equipped with a selective $^{19}F/^{1}H$ probe. Each spectrum was recorded at 25° C. in buffers with a 90:10 $H_2O$: $D_2O$ ratio. All spectra were collected with a sweep width of 5 ppm and an acquisition time of 20 minutes. The LF assay was performed with 10 μM recombinant LF (List Biological Laboratories) and 20 μM of peptide substrate Ac-A-R-R-K-K-V-Y-P-NH-Ph-$CF_3$ (Anaspec); inhibition activity was detected in the same condition using 20 μM of inhibitor. Reaction was quenched after 30 minutes using 100 μM GM6001 (List Biological Laboratories) at 0° C.

The invention has been described with reference to various specific and preferred embodiments and techniques. However, it should be understood that many variations and modifications may be made while remaining within the spirit and scope of the invention.

All patents, patent applications, and literature cited in the specification are hereby incorporated by reference in their entirety. In the case of any inconsistencies, the present disclosure, including any definitions therein will prevail.

The invention claimed is:

1. A therapeutic method to treat anthrax comprising inhibiting lethal factor protease activity of anthrax toxin in a mammal in need of such therapy, by administering an effective inhibitory amount of a compound of formula (I):

I

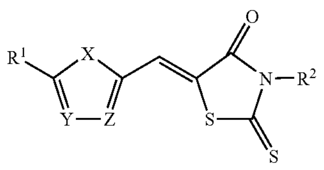

wherein $R^1$ is hydrogen or phenyl, optionally substituted with 1, or 2 substituents independently selected from halo, —$NO_2$, —COOH, or —$SO_2NH_2$;

wherein $R^2$ is —$CH_2COOH$, or a pharmaceutical acceptable salt thereof;

wherein,

X is O, NH, S or $CH_2$;

Y is N or CH; and

Z is N or CH.

2. The method of claim 1 wherein $R^1$ is nitrophenyl, halophenyl, dihalophenyl, carboxy-phenyl, or halonitrophenyl.

3. The method of claim 1 wherein $R^1$ is dichlorophenyl, fluorophenyl, iodophenyl, carboxy-phenyl, chlorocarboxy-phenyl, or halonitrophenyl.

4. A therapeutic method to treat anthrax comprising inhibiting lethal factor protease activity of anthrax toxin in a mammal in need of such therapy, by administering an effective inhibitory amount of at least one compound of formula:

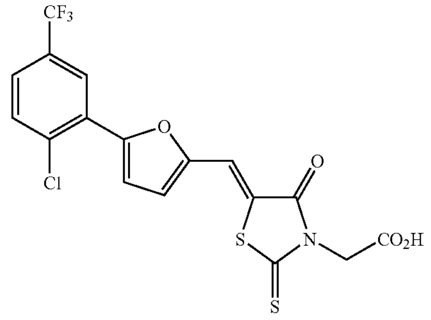

or

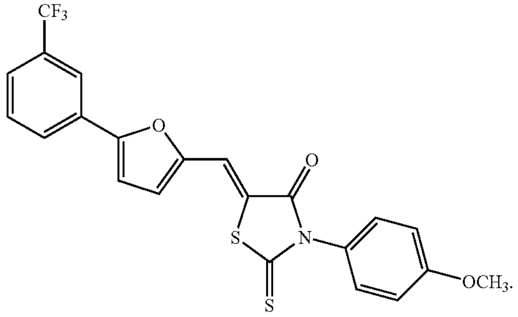

5. A therapeutic method to treat anthrax comprising inhibiting lethal factor protease activity of anthrax toxin in a mammal in need of such therapy by administering an effective inhibitory amount of a compound of formula (II):

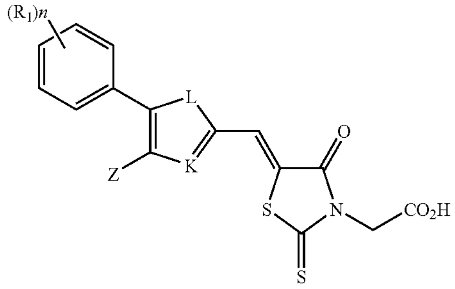

(II)

wherein each $R^1$ is independently alkyl, alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, cyano, $COOR_7$, $C(O)R_7$, $NR_7R_8$ or —X—Y—Z;

each Z is independently hydrogen, aryl, heteroaryl, heterocycle or cycloalkyl; optionally substituted with 1, 2 or 3 alkyl, alkoxy, halo, haloalkyl, hydroxy, hydroxyalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $COOR_7$, $C(O)R_7$, or $NR_7R_8$;

X is O, CO, NH, S or $CH_2$;

Y is O, CO, NH, S or $CH_2$;

L is O, S or NH;

K is N or CH;

each $R_7$ and $R_8$ are independently hydrogen, alkyl or aryl; and n is 1, 2, 3, 4 or 5;

or a pharmaceutically acceptable salt thereof.

6. A therapeutic method to treat anthrax comprising inhibiting lethal factor protease activity of anthrax toxin in a mammal in need of such therapy, by administering an effective inhibitory amount of a compound of formula (I):

(I)

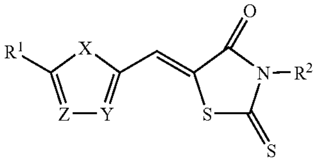

wherein $R^1$ is hydrogen or phenyl, optionally substituted with 1 or 2 substituents independently selected from halo, $—NO_2$, or $—SO_2NH_2$;

$R^2$ is $—(CH_2)_{1-3}COOH$, or a pharmaceutically acceptable salt thereof; and wherein, X is O, NH, S or $CH_2$;

Y is N or CH; and

Z is N or CH.

* * * * *

UNITED STATES PATENT AND TRADEMARK OFFICE

CERTIFICATE OF CORRECTION

PATENT NO. : 7,718,680 B2
APPLICATION NO. : 11/233924
DATED : May 18, 2010
INVENTOR(S) : Maurizio Pellecchia et al.

It is certified that error appears in the above-identified patent and that said Letters Patent is hereby corrected as shown below:

In column 2, line 35, delete "$-C_4$alkenyl," and insert -- $-C_{1\text{-}4}$alkenyl, --, therefor.

In column 2, line 37, delete "furyl$C_{1\text{-}3}$ alkylene-," and insert -- furyl$C_{1\text{-}3}$alkylene-, --, therefor.

In column 3, line 13, delete "Co," and insert -- CO, --, therefor.

In column 3, lines 44–45, delete "BCL-$X_L$," and insert -- BcL-$X_L$, --, therefor.

In column 3, line 46, delete "BCL-$X_L$." and insert -- BcL-$X_L$. --, therefor.

In column 16, line 35, delete "J" and insert -- J. --, therefor.

In column 16, line 58, delete "et a." and insert -- et al. --, therefor.

In column 18, line 35, delete "$R^2$" and insert -- $R^2$. --, therefor.

In column 21, line 44, delete "five-membered." and insert -- five-membered --, therefor.

In column 22, line 63, delete "Derivatives-Based" and insert -- Derivatives Based --, therefor.

In column 23, line 38, delete "(COMFA)" and insert -- (CoMFA) --, therefor.

In column 39, line 22, in Claim 5, delete "$C(O)R_7$," and insert -- $C(=O)R_7$, --, therefor.

In column 39, line 29, in Claim 5, after "carboxyalkyl," delete "keto, thioxo,".

In column 39, line 30, in Claim 5, delete "$C(O)R_7$," and insert -- $C(=O)R_7$, --, therefor.

Signed and Sealed this

Sixth Day of July, 2010

David J. Kappos

*Director of the United States Patent and Trademark Office*